US009623222B2

(12) United States Patent
McKay

(10) Patent No.: US 9,623,222 B2
(45) Date of Patent: Apr. 18, 2017

(54) DRUG DEPOT WITH ANCHOR

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1303 days.

(21) Appl. No.: 12/261,956

(22) Filed: Oct. 30, 2008

(65) Prior Publication Data

US 2010/0112034 A1    May 6, 2010

(51) Int. Cl.
   *A61F 2/04*    (2013.01)
   *A61M 31/00*   (2006.01)
   *A61K 9/00*    (2006.01)
   *A61M 37/00*   (2006.01)

(52) U.S. Cl.
   CPC ......... *A61M 31/002* (2013.01); *A61K 9/0024* (2013.01); *A61M 37/0069* (2013.01)

(58) Field of Classification Search
   CPC ............ A61K 9/0024; A61M 37/0069; A61M 31/002
   USPC ................................................ 424/426, 423
   See application file for complete search history.

(56) References Cited

U.S. PATENT DOCUMENTS

| | | | |
|---|---|---|---|
| 4,624,255 A | 11/1986 | Schenck et al. | |
| 4,863,457 A | 9/1989 | Lee | |
| 5,522,844 A | 6/1996 | Johnson | |
| 5,707,643 A | 1/1998 | Ogura et al. | |
| 5,868,789 A | 2/1999 | Huebner | |
| 6,471,689 B1 | 10/2002 | Joseph et al. | |
| 6,756,058 B2 | 6/2004 | Brubaker et al. | |
| 6,974,462 B2 | 12/2005 | Sater | |
| 7,144,412 B2 | 12/2006 | Wolf et al. | |
| 7,166,570 B2 | 1/2007 | Hunter et al. | |
| 7,220,281 B2 | 5/2007 | Lambrecht et al. | |
| 7,229,441 B2 | 6/2007 | Trieu et al. | |
| 7,235,043 B2 | 6/2007 | Gellman et al. | |
| 7,318,840 B2 | 1/2008 | McKay | |
| 7,329,259 B2 | 2/2008 | Cragg | |
| 7,361,168 B2 | 4/2008 | Makower et al. | |
| 7,367,978 B2 | 5/2008 | Drewry | |
| 2002/0016602 A1* | 2/2002 | Li et al. ........................ 606/139 |
| 2003/0118649 A1* | 6/2003 | Gao ..................... A61K 9/0024 |
| | | | 424/471 |
| 2003/0171401 A1 | 9/2003 | Johnson et al. | |
| 2003/0204191 A1 | 10/2003 | Sater et al. | |
| 2004/0151753 A1* | 8/2004 | Chen et al. ................... 424/426 |
| 2006/0106361 A1 | 5/2006 | Muni et al. | |
| 2006/0178702 A1* | 8/2006 | Pierce et al. .................. 606/232 |
| 2007/0179623 A1* | 8/2007 | Trieu et al. ................ 623/17.16 |
| 2007/0185497 A1 | 8/2007 | Cauthen et al. | |
| 2007/0243225 A1* | 10/2007 | McKay ........................ 424/423 |
| 2007/0243228 A1 | 10/2007 | McKay | |

FOREIGN PATENT DOCUMENTS

WO        2007121288        10/2007

OTHER PUBLICATIONS

Sibert, PNAS 91, 25, 1994 (abstract).*
International Search Report and Written Opinion for US Application PCT/US2009/062591 mailed on Jun. 22, 2010.

* cited by examiner

*Primary Examiner* — Susan Tran
*Assistant Examiner* — William Craigo

(57) ABSTRACT

A drug depot implantable at or near a target tissue site beneath the skin of a patient is provided, the drug depot comprising a therapeutically effective amount of a drug; at least one line having a distal end and a proximal end, the proximal end of the line attached to the drug depot; an anchor attached to the distal end of the line and configured to limit movement of the drug depot at or near the target tissue site, wherein the drug depot is capable of releasing the therapeutically effective amount of the drug over a period of at least one day. In some embodiments, the drug depot provided can include an effective amount of at least analgesic and/or at least one anti-inflammatory agent at or near a target site, and can reduce, prevent or treat inflammation and/or pain.

20 Claims, 6 Drawing Sheets

DRUG DEPOT WITH ANCHOR

BACKGROUND

Drugs may be delivered to patients by a variety of methods including oral, intravenous, intramuscular, inhalation, topical, subcutaneous delivery or delivery directly or locally to the treatment site (e.g., intrathecally, intraspinally, intraarticularly, etc.). The method of delivery chosen depends, among other things, upon the condition being treated, desired therapeutic concentration of the drug to be achieved in the patient and the duration of drug concentration that must be maintained.

Recently, drug depots have been developed which allow a drug to be introduced or administered to sites beneath the skin of a patient so that the drug is slowly released over a long period of time. Such drug depots allow the drug to be released from the depot in a relatively uniform dose over weeks, months or even years. This method of administering drugs is becoming especially important for contraceptives and cancer drugs that are implanted subcutaneously.

Sometimes, after the drug depot is implanted at the treatment site, the drug depot may migrate from the implant site prior to surgical closure (e.g., floats off in blood or shifts as tissues are repositioned during surgical site closure) or as physiological conditions change (e.g., repair and regeneration of cells, tissue ingrowth, movement at implant site, etc.). At times, this may reduce efficacy of the drug as the drug depot migrates away from the implant site and lodges in a distant site. If this occurs, the drug depot will have to be removed from the distant site and have to be reinserted causing additional physical and psychological trauma to a patient. In some cases, if the drug depot migrates into a joint, the drug depot may inhibit movement. In more severe cases, if the drug depot migrates, it may restrict blood flow causing an ischemic event (e.g., embolism, necrosis, infarction, etc.), which could be detrimental to the patient.

Postoperative pain tends to be a difficult condition to treat and may be detrimental to the patient if not properly treated. The site of the surgery has a profound effect upon the degree of postoperative pain a patient may suffer. In general, operations on the thorax and upper abdomen are more painful than operations on the lower abdomen, which in turn are more painful than peripheral operations on the limbs. However, any operation involving a body cavity, large joint surfaces, the spine or deep tissues should be regarded as painful. In particular, operations on the thorax or upper abdomen may produce widespread changes in pulmonary function, an increase in abdominal muscle tone and an associated decrease in diaphragmatic function. The result will be an inability to cough and clear secretions, which may lead to lung collapse and pneumonia. Prolonged pain can reduce physical activity and lead to venous stasis and an increased risk of deep vein thrombosis and consequently pulmonary embolism. In addition, there can be widespread effects on gut and urinary tract motility, which may lead in turn to postoperative ileus, nausea, vomiting and urinary retention. These problems are unpleasant for the patient and may prolong hospital stay and are exacerbated if after implantation the drug depot migrates away from the implant site.

New drug depot compositions and methods are needed, which can easily allow accurate and precise placement of a drug depot. When implanting several drug depots at a time, drug depot compositions and methods are needed that accurately and precisely allow placement of the drug depot in a manner that optimizes location, accurate spacing, and drug distribution.

SUMMARY

A new implantable drug depot that improves drug efficacy and reduces unwanted migration of the drug depot is provided. In various embodiments, new drug depot compositions and methods are provided that effectively prevent, treat or reduce postoperative pain and/or inflammation by providing consistent analgesic and/or anti-inflammatory efficacy at the target tissue site of pain generation. In various embodiments, the drug depot is attached to an anchor by a line (e.g., a suture), which reduces or prevents the drug depot from migrating away from the implant site prior to surgical closure.

In various embodiments, the drug depot is suitable for implantation at or near an annular tear near an intervertebral disc, where the anchor will be implanted in, at, or near the annular tear and the drug depot will be positioned so as to provide effective pain and/or inflammation relief by the annular tear.

In one embodiment, a drug depot is provided implantable at or near a target tissue site beneath the skin of a patient, the drug depot comprising a therapeutically effective amount of a drug; at least one line having a distal end and a proximal end, the proximal end of the line attached to the drug depot; an anchor attached to the distal end of the line and configured to limit movement of the drug depot at or near the target tissue site, wherein the drug depot is capable of releasing the therapeutically effective amount of the drug over a period of at least one day.

In another embodiment, a drug depot is provided implantable at or near a target tissue site beneath the skin of a patient, the drug depot comprising a therapeutically effective amount of a drug; at least one suture having a distal end and a proximal end, the proximal end of the suture attached to the drug depot; an anchor attached to the distal end of the suture and configured to limit movement of the drug depot at or near the target tissue site, wherein the drug depot is capable of releasing the therapeutically effective amount of the drug over a period of at least one day.

In one exemplary embodiment, a method is provided for treating or preventing pain or inflammation in a patient in need of such treatment, the method comprising implanting one or more biodegradable drug depots comprising a therapeutically effective amount of an analgesic and/or anti-inflammatory agent at or near a target tissue site beneath the skin, wherein the one or more drug depots comprise at least one biodegradable suture having a distal end and a proximal end, the proximal end of the at least one suture attached to the one or more drug depots; a biodegradable anchoring pellet attached to the distal end of the at least one suture and configured to limit movement of the one or more drug depots at or near the target tissue site, wherein the drug depot is capable of releasing the therapeutically effective amount of the drug over a period of at least three days.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Figure 1A:
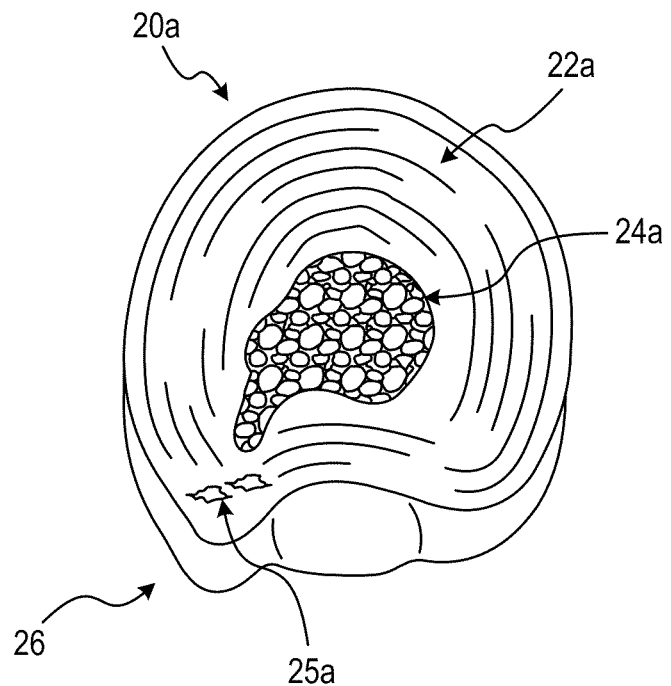
FIG. 1A is a cross-sectional view of a target tissue site, which is a herniated intervertebral disc where the disc has not ruptured.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

The headings below are not meant to limit the disclosure in any way; embodiments under any one heading may be used in conjunction with embodiments under any other heading.

DEFINITIONS

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

"Analgesic" refers to an agent or compound that can reduce, relieve or eliminate pain. Examples of analgesic agents include but are not limited to acetaminophen, a local anesthetic, such as for example, lidocaine, bupivicaine, ropivacaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, levorphanol, mepiridine, methadone, morphine, nalbuphine, opium, oxycodone, papaveretum, pentazocine, pethidine, phenoperidine, piritramide, dextropropoxyphene, remifentanil, sufentanil, tilidine, tramadol, codeine, dihydrocodeine, meptazinol, dezocine, eptazocine, flupirtine or a combination thereof.

The phrase "anti-inflammatory agent" refers to an agent or compound that has anti-inflammatory effects. These agents may remedy pain by reducing inflammation. Examples of anti-inflammatory agents include, but are not limited to, a statin, sulindac, sulfasalazine, naroxyn, diclofenac, indomethacin, ibuprofen, flurbiprofen, ketoprofen, aclofenac, aloxiprin, aproxen, aspirin, diflunisal, fenoprofen, mefenamic acid, naproxen, phenylbutazone, piroxicam, meloxicam, salicylamide, salicylic acid, desoxysulindac, tenoxicam, ketoralac, clonidine, flufenisal, salsalate, triethanolamine salicylate, aminopyrine, antipyrine, oxyphenbutazone, apazone, cintazone, flufenamic acid, clonixeril, clonixin, meclofenamic acid, flunixin, colchicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, triflumidate, fenamates (mefenamic acid, meclofenamic acid), nabumetone, celecoxib, etodolac, nimesulide, apazone, gold, tepoxalin; dithiocarbamate, or a combination thereof. Anti-inflammatory agents also include other compounds such as steroids, such as for example, fluocinolone, cortisol, cortisone, hydrocortisone, fludrocortisone, prednisone, prednisolone, methylprednisolone, triamcinolone, betamethasone, dexamethasone, beclomethasone, fluticasone interleukin-1 receptor antagonists, thalidomide (a TNF-α release inhibitor), thalidomide analogues (which reduce TNF-α production by macrophages), bone morphogenetic protein (BMP) type 2 or BMP-4 (inhibitors of caspase 8, a TNF-α activator), quinapril (an inhibitor of angiotensin II, which upregulates TNF-α), interferons such as IL-11 (which modulate TNF-α receptor expression), and aurin-tricarboxylic acid (which inhibits TNF-α), guanidinoethyldisulfide, or a combination thereof.

Exemplary anti-inflammatory agents include, for example, naproxen; diclofenac; celecoxib; sulindac; diflunisal; piroxicam; indomethacin; etodolac; meloxicam; ibuprofen; ketoprofen; r-flurbiprofen; mefenamic; nabumetone; tolmetin, and sodium salts of each of the foregoing; ketorolac bromethamine; ketorolac tromethamine; ketorolac acid; choline magnesium trisalicylate; rofecoxib; valdecoxib; lumiracoxib; etoricoxib; aspirin; salicylic acid and its sodium salt; salicylate esters of alpha, beta, gamma-tocopherols and tocotrienols (and all their d, 1, and racemic isomers); methyl, ethyl, propyl, isopropyl, n-butyl, sec-butyl, t-butyl, esters of acetylsalicylic acid; tenoxicam; aceclofenac; nimesulide; nepafenac; amfenac; bromfenac; flufenamate; phenylbutazone, or a combination thereof.

Exemplary steroids include, for example, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, dexamethasone 21-acetate, dexamethasone 21-phosphate di-Na salt, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide or a combination thereof.

Examples of a useful statin for treatment of pain and/or inflammation include, but is not limited to, atorvastatin, simvastatin, pravastatin, cerivastatin, mevastatin (see U.S. Pat. No. 3,883,140, the entire disclosure is herein incorporated by reference), velostatin (also called synvinolin; see U.S. Pat. Nos. 4,448,784 and 4,450,171 these entire disclosures are herein incorporated by reference), fluvastatin, lovastatin, rosuvastatin and fluindostatin (Sandoz XU-62-320), dalvastain (EP Appln. Publn. No. 738510 A2, the entire disclosure is herein incorporated by reference), eptastatin, pitavastatin, or pharmaceutically acceptable salts thereof or a combination thereof. In various embodiments, the statin may comprise mixtures of (+)R and (−)-S enantiomers of the statin. In various embodiments, the statin may comprise a 1:1 racemic mixture of the statin. Anti-inflammatory agents also include those with anti-inflammatory properties, such as, for example, amitriptyline, carbamazepine, gabapentin, pregabalin, clonidine, or a combination thereof.

Unless otherwise specified or apparent from context, where this specification and the set of claims that follows refer to a drug (e.g., an anti-inflammatory agent, analgesic, and the like) the inventor(s) are also referring to a pharmaceutically acceptable salt of the drug including stereoisomers. Pharmaceutically acceptable salts include those salt-forming acids and bases that do not substantially increase the toxicity of the compound. Some examples of potentially suitable salts include salts of alkali metals such as magnesium, calcium, sodium, potassium and ammonium, salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, or the like.

"Treating" or treatment of a disease or condition refers to executing a protocol, which may include administering one or more drugs to a patient (human, normal or otherwise, or other mammal), in an effort to alleviate signs or symptoms of the disease. Alleviation can occur prior to signs or symptoms of the disease or condition appearing, as well as after their appearance. Thus, "treating" or "treatment" includes "preventing" or "prevention" of disease or undesirable condition. In addition, "treating" or "treatment" does not require complete alleviation of signs or symptoms, does not require a cure, and specifically includes protocols that have only a marginal effect on the patient. "Reducing pain" includes a decrease in pain and does not require complete alleviation of pain signs or symptoms, and does not require a cure. In various embodiments, reducing pain includes even a marginal decrease in pain. By way of example, the administration of the effective dosages of at least one analgesic agent and at least one anti-inflammatory agent may be used to prevent, treat or relieve the symptoms of pain and/or inflammation.

"Localized" delivery includes delivery where one or more drugs are deposited within a tissue, for example, a nerve root of the nervous system or a region of the brain, or in close proximity (within about 5 cm, or preferably within about 2 cm, for example) thereto. A "targeted delivery system" provides delivery of one or more drugs depots having a quantity of therapeutic agent that can be deposited at or near the target site as needed for treatment of pain, inflammation or other disease or condition.

The term "mammal" refers to organisms from the taxonomy class "mammalian," including but not limited to humans, other primates such as chimpanzees, apes, orangutans and monkeys, rats, mice, cats, dogs, cows, horses, etc. In various embodiments, the mammal is a human patient.

Drug Depot

In some embodiments, a drug depot implantable at or near a target tissue site beneath the skin of a patient is provided, the drug depot comprising a therapeutically effective amount of a drug and an anchor attached to the drug depot by a line. The anchor limits movement of the drug depot at or near the target tissue site, wherein at least one region of the drug depot is capable of releasing the therapeutically effective amount of the drug over a period of at least one day.

A "drug depot" comprises the composition in which at least one active pharmaceutical ingredient or drug is administered to the body. Thus, a drug depot may comprise a physical structure to facilitate implantation and retention in a desired site (e.g., a disc space, a spinal canal, a tissue of the patient, particularly at or near a site of surgery, pain, or site of inflammation, etc.). The drug depot also comprises the drug itself. The term "drug" as used herein is generally meant to refer to any substance that alters the physiology of a patient. The term "drug" may be used interchangeably herein with the terms "therapeutic agent," "therapeutically effective amount," and "active pharmaceutical ingredient" or "API." It will be understood that unless otherwise specified a "drug" formulation may include more than one therapeutic agent, wherein exemplary combinations of therapeutic agents include a combination of two or more drugs. The drug provides a concentration gradient of the therapeutic agent for delivery to the site. In various embodiments, the drug depot provides an optimal drug concentration gradient of the therapeutic agent at a distance of up to about 0.1 cm to about 5 cm from the implant site, and comprises at least one anti-inflammatory agent or its pharmaceutically acceptable salt and/or at least one analgesic agent or its pharmaceutically acceptable salt.

A "depot" includes but is not limited to capsules, coatings, matrices, wafers, sheets, strips, ribbons, pills, pellets, or other pharmaceutical delivery or a combination thereof. Suitable materials for the depot are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof. Typically, the depot will be a solid or semi-solid formulation comprised of a biocompatible material that can be biodegradable. The term "solid" is intended to mean a rigid material, while "semi-solid" is intended to mean a material that has some degree of flexibility, thereby allowing the depot to bend and conform to the surrounding tissue requirements.

A "therapeutically effective amount" or "effective amount" is such that when administered, the drug results in alteration of the biological activity, such as, for example, inhibition of inflammation, reduction or alleviation of pain, improvement in the condition through muscle relaxation, etc. The dosage administered to a patient can unless otherwise specified or apparent from context be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired. In some embodiments the formulation of the drug depot is designed for immediate release. In other embodiments the formulation is designed for sustained release. In other embodiments, the formulation comprises one or more immediate release surfaces and one or more sustain release surfaces.

The phrases "sustained release" or "sustain release" (also referred to as extended release or controlled release) are used herein to refer to one or more therapeutic agent(s) that is introduced into the body of a human or other mammal and continuously or continually releases a stream of one or more therapeutic agents over a predetermined time period and at a therapeutic level sufficient to achieve a desired therapeutic effect throughout the predetermined time period. Reference to a continuous or continual release stream is intended to encompass release that occurs as the result of biodegradation in vivo of the drug depot, or a matrix or component thereof, or as the result of metabolic transformation or dissolution of the therapeutic agent(s) or conjugates of therapeutic agent(s). As persons of ordinary skill are aware, sustained release formulations may, by way of example, be created as films, slabs, pellets, microparticles, microspheres, microcapsules, spheroids, shaped derivatives and paste. Further, the formulations may be used in conjunction with any implantable, or insertable system that a person of ordinary skill would appreciate as useful in connection with embodiments herein including but not limited to parenteral formulations, microcapsules, pastes, implantable rods, pellets, plates or fibers, etc.

The phrase "immediate release" is used herein to refer to one or more therapeutic agent(s) that is introduced into the body and that is allowed to dissolve in or become absorbed at the location to which it is administered, with no intention of delaying or prolonging the dissolution or absorption of the drug. Immediate release refers to the release of drug within a short time period following administration, e.g., generally within a few minutes to about 1 to 2 hours.

The phrase "release rate profile" refers to the percentage of active ingredient that is released over fixed units of time, e.g., mcg/hr, mcg/day, mg/hr, mg/day, 10% per day for ten days, and the like. As persons of ordinary skill know, a release rate profile may be but need not be linear. By way of a non-limiting example, the drug depot may be a pellet that releases at least one analgesic agent in a bolus dose and at least one anti-inflammatory agent over a period of time.

The term "biodegradable" includes that all or parts of the drug depot will degrade over time by the action of enzymes, by hydrolytic action and/or by other similar mechanisms in the human body. In various embodiments, "biodegradable" includes that the depot can break down or degrade within the body to non-toxic components after or while a therapeutic agent has been or is being released. By "bioerodible" it is meant that the depot will erode or degrade over time due, at least in part, to contact with substances found in the surrounding tissue, fluids or by cellular action. By "bioabsorbable" it is meant that the depot will be broken down and absorbed within the human body, for example, by a cell or tissue. "Biocompatible" means that the depot will not cause substantial tissue irritation or necrosis at the target tissue site.

The depot and/or anchor may comprise non-biodegradable material. Examples of non-biodegradable polymers include, but are not limited to, various cellulose derivatives (carboxymethyl cellulose, cellulose acetate, cellulose acetate propionate, ethyl cellulose, hydroxypropyl methyl cellulose, hydroxyalkyl methyl celluloses, and alkyl celluloses), silicon and silicon-based polymers (such as polydimethylsiloxane), polyethylene-co-(vinyl acetate), poloxamer, polyvinylpyrrolidone, poloxamine, polypropylene, polyamide, polyacetal, polyester, poly ethylene-chlorotrifluoro-ethylene, polytetrafluoroethylene (PTFE or "Teflon™"), styrene butadiene rubber, polyethylene, polypropylene, polyphenylene oxide-polystyrene, poly-α-chloro-p-xylene, polymethylpentene, polysulfone, non-degradable ethylene-vinyl acetate (e.g., ethylene vinyl acetate disks and poly (ethylene-co-vinyl acetate)), and other related biostable polymers.

Non-resorbable polymers can also include, but are not limited to, delrin, polyurethane, copolymers of silicone and polyurethane, polyolefins (such as polyisobutylene and polyisoprene), acrylamides (such as polyacrylic acid and poly(acrylonitrile-acrylic acid)), neoprene, nitrile, acrylates (such as polyacrylates, poly(2-hydroxy ethyl methacrylate), methyl methacrylate, 2-hydroxyethyl methacrylate, and copolymers of acrylates with N-vinyl pyrrolidone), N-vinyl lactams, polyacrylonitrile, glucomannan gel, vulcanized rubber and combinations thereof. Examples of polyurethanes include thermoplastic polyurethanes, aliphatic polyurethanes, segmented polyurethanes, hydrophilic polyurethanes, polyether-urethane, polycarbonate-urethane and silicone polyether-urethane. Other suitable non-resorbable material include, but are not limited to, lightly or highly cross-linked biocompatible homopolymers and copolymers of hydrophilic monomers such as 2-hydroxyalkyl acrylates and methacrylates, N-vinyl monomers, and ethylenically unsaturated acids and bases; polycyanoacrylate, polyethylene oxide-polypropylene glycol block copolymers, polygalacturonic acid, polyvinyl pyrrolidone, polyvinyl acetate, polyalkylene glycols, polyethylene oxide, collagen, sulfonated polymers, vinyl ether monomers or polymers, alginate, polyvinyl amines, polyvinyl pyridine, and polyvinyl imidazole. Depending on the amount of crosslinking within the bioresorbable polymers, the degradation time of the polymer can be reduced, thus making the polymer, for the purpose of this invention, appear to be non-resorbable over the time frame of the use of the material for this invention.

The phrase "pain management medication" includes one or more therapeutic agents that are administered to prevent, alleviate or remove pain entirely. These include anti-inflammatory agents, muscle relaxants, analgesics, anesthetics, narcotics, and so forth, and combinations thereof.

In various embodiments, the depot can be designed to cause an initial burst dose of one or more therapeutic agents within the first 24 hours after implantation. "Initial burst" or "burst effect" or "bolus dose" or "pulse dose" refer to the release of therapeutic agent from the depot during the first 24 hours after the depot comes in contact with an aqueous fluid (e.g., synovial fluid, cerebral spinal fluid, etc.). The burst effect may be an immediate release. The "burst effect" is believed to be due to the increased release of therapeutic agent from the depot. The initial burst effect or bolus dose may be determined beforehand by formulating the depot by calculating the quotient obtained by dividing (i) the effective amount by weight of therapeutic agent to be released from the depot or region in a predetermined initial period of time after implantation of the depot, by (ii) the total amount of therapeutic agent that is to be delivered from an implanted composition. It is understood that the initial burst may vary depending on the shape and surface area of the implant.

The burst effect with respect to the region or depot, in various embodiments, can be designed so that a larger initial dose may be released over a short period of time to achieve the desired effect. For example, if a drug depot is designed to release 15 mg of morphine per 48 hours, then the initial burst dose or bolus dose region or depot will be designed to release a percentage of the dose within the first 24 hours (e.g., 10 mg of morphine or 66% of the 48 hour dose within 24 hours). Thus, the burst effect of the drug depot or region releases more therapeutic agent than the sustained release region or depot.

A region or depot that utilizes a burst effect or bolus dose will release more therapeutic agent (e.g., analgesic and/or anti-inflammatory) than the sustained release region or depot. For example, particularly with painful chronic conditions including rheumatoid arthritis, osteoarthritis, a spinal disc herniation (e.g., sciatica), carpal/tarsal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, spondilothesis, stenosis, discogenic back pain, and joint pain or the like, the initial burst effect of the drug depot or region of the drug depot will be advantageous as it will provide more immediate pain and/or inflammation relief as a bolus dose of drug will be released at or near the target tissue site and provide the desired reducing, or alleviation of signs or symptoms of pain and/or inflammation. For example, the drug depot or region of the drug depot may release 51%, 52%, 53%, 54%, 55%, % 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% of the daily dose within the first one to twelve hours to reduce, prevent or treat pain and/or inflammation. The pain and/or inflammation may also be postoperative pain following surgery.

The drug depot can comprise at least one analgesic agent or its pharmaceutically acceptable salt and/or at least one anti-inflammatory agent or its pharmaceutically acceptable salt may be co-administered with a muscle relaxant. Co-administration may involve administering at the same time in separate drug depots or formulating together in the same drug depot.

Exemplary muscle relaxants include by way of example and not limitation, alcuronium chloride, atracurium bescylate, baclofen, carbolonium, carisoprodol, chlorphenesin carbamate, chlorzoxazone, cyclobenzaprine, dantrolene, decamethonium bromide, fazadinium, gallamine triethiodide, hexafluorenium, meladrazine, mephensin, metaxalone, methocarbamol, metocurine iodide, pancuronium, pridinol mesylate, styramate, suxamethonium, suxethonium, thiocolchicoside, tizanidine, tolperisone, tubocuarine, vecuronium, or combinations thereof.

The drug depot may also comprise other therapeutic agents or active ingredients in addition to the at least one analgesic agent or its pharmaceutically acceptable salt and at least one anti-inflammatory agent or its pharmaceutically acceptable salt. Suitable additional therapeutic agents include, but are not limited to, integrin antagonists, alpha-4 beta-7 integrin antagonists, cell adhesion inhibitors, interferon gamma antagonists, CTLA4-Ig agonists/antagonists (BMS-188667), CD40 ligand antagonists, Humanized anti-IL-6 mAb (MRA, Tocilizumab, Chugai), HMGB-1 mAb (Critical Therapeutics Inc.), anti-IL2R antibodies (daclizumab, basilicimab), ABX (anti IL-8 antibodies), recombinant human IL-10, or HuMax IL-15 (anti-IL 15 antibodies).

Other suitable therapeutic agents that may be co-administered with the anti-inflammatory agent and analgesic agent include IL-1 inhibitors, such Kineret® (anakinra) which is a recombinant, non-glycosylated form of the human inerleukin-1 receptor antagonist (IL-IRa), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. It is contemplated that where desirable a pegylated form of the above may be used. Examples of other therapeutic agents include NF kappa B inhibitors such as glucocorticoids, antioxidants, such as dilhiocarbamate.

Specific examples of additional therapeutic agents suitable for use include, but are not limited to, an anabolic growth factor or anti-catabolic growth factor, analgesic agent, or an osteoinductive growth factor or a combination thereof.

Suitable anabolic growth or anti-catabolic growth factors include, but are not limited to, a bone morphogenetic protein, a growth differentiation factor, a LIM mineralization protein, CDMP or progenitor cells or a combination thereof.

Suitable analgesic agents include, but are not limited to, acetaminophen, bupivicaine, opioid analgesics such as amitriptyline, carbamazepine, gabapentin, pregabalin, clonidine, opioid analgesics or a combination thereof. Opioid analgesics include, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, tramadol or a combination thereof.

For each of the anti-inflammatory agents and analgesic agents, in some embodiments, the release of each compound may be for at least one, at least two, at least three, at least four, at least five, at least six, at least seven, at least eight, at least nine, at least ten, at least eleven, at least twelve, at least thirteen, at least fourteen, or at least fifteen days, or longer.

The drug depot may also be administered with non-active ingredients. These non-active ingredients may have multifunctional purposes including the carrying, stabilizing and controlling the release of the therapeutic agent(s). The sustained release process, for example, may be by a solution-diffusion mechanism or it may be governed by an erosion-sustained process.

In various embodiments, the non-active ingredients will be durable within the tissue site for a period of time equal to (for biodegradable components) or greater than (for non-biodegradable components) the planned period of drug delivery. For example, the depot material may have a melting point or glass transition temperature close to or higher than body temperature, but lower than the decomposition or degradation temperature of the therapeutic agent. However, the pre-determined erosion of the depot material can also be used to provide for slow release of the loaded therapeutic agent(s).

In various embodiments, the drug depot, line, and/or anchor may not be biodegradable or comprise material that is not biodegradable. Non-biodegradable polymers include, but are not limited to, various cellulose derivatives (carboxymethyl cellulose, cellulose acetate, cellulose acetate propionate, ethyl cellulose, hydroxypropyl methyl cellulose, hydroxyalkyl methyl celluloses, and alkyl celluloses), silicon and silicon-based polymers (such as polydimethylsiloxane), polyethylene-co-(vinyl acetate), poloxamer, polyvinylpyrrolidone, poloxamine, polypropylene, polyamide, polyacetal, polyester, poly ethylene-chlorotrifluoroethylene, polytetrafluoroethylene (PTFE or "Teflon™"), styrene butadiene rubber, polyethylene, polypropylene, polyphenylene oxide-polystyrene, poly-α-chloro-p-xylene, polymethylpentene, polysulfone, non-degradable ethylene-vinyl acetate (e.g., ethylene vinyl acetate disks and poly(ethylene-co-vinyl acetate)), and other related biostable polymers or combinations thereof.

The drug depot, line, and/or anchor may comprise non-resorbable polymers as well. These non-resorbable polymers can include, but are not limited to, delrin, polyurethane, copolymers of silicone and polyurethane, polyolefins (such as polyisobutylene and polyisoprene), acrylamides (such as polyacrylic acid and poly(acrylonitrile-acrylic acid)), neoprene, nitrile, acrylates (such as polyacrylates, poly(2-hydroxy ethyl methacrylate), methyl methacrylate, 2-hydroxyethyl methacrylate, and copolymers of acrylates with N-vinyl pyrrolidone), N-vinyl lactams, polyacrylonitrile, glucomannan gel, vulcanized rubber and combinations thereof. Examples of polyurethanes include thermoplastic polyurethanes, aliphatic polyurethanes, segmented polyurethanes, hydrophilic polyurethanes, polyether-urethane, polycarbonate-urethane and silicone polyether-urethane. Typically, the non-degradable drug depots may need to be removed.

In some instance, it may be desirable to avoid having to remove the drug depot, line, and/or anchor after use. In those instances, the depot, line, and/or anchor may comprise a biodegradable material. There are numerous materials available for this purpose and having the characteristic of being able to breakdown or disintegrate over a prolonged period of time when positioned at or near the target tissue. As a function of the chemistry of the biodegradable material, the mechanism of the degradation process can be hydrolytical or enzymatical in nature, or both. In various embodiments, the degradation of the drug depot, line, and/or anchor can occur either at the surface (heterogeneous or surface erosion) or uniformly throughout the drug depot, line, and/or anchor (homogeneous or bulk erosion).

In various embodiments, the depot may comprise a bioabsorbable, and/or a biodegradable biopolymer that may provide immediate release, or sustained release of the at least one analgesic agent and at least one anti-inflammatory agent. Examples of suitable sustained release biopolymers include but are not limited to poly (alpha-hydroxy acids), poly (lactide-co-glycolide) (PLGA or PLG), polylactide (PLA), polyglycolide (PG), polyethylene glycol (PEG) conjugates of poly (alpha-hydroxy acids), polyorthoesters, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, poly(glycolide-,-caprolactone), ,-caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof. As persons of ordinary skill are aware, mPEG may be used as a plasticizer for PLGA, but other polymers/excipients may be used to achieve the same effect. mPEG imparts malleability to the resulting formulations.

Where different combinations of polymers are used (bi, tri (e.g., PLGA-PEO-PLGA) or terpolymers), they may be used in different molar ratios, 1:1, 2:1, 3:1, 4:1, 5:1, 6:1, 7:1, 8:1, 9:1, or 10:1. For example, for a 130-day release drug depot, the polymer make up is 50:50 PLGA to 100 PLA. The molecular weight range is 0.45 to 0.8 dI/g.

In various embodiments, the molecular weight of the polymer can be a wide range of values. The average molecular weight of the polymer can be from about 1000 to about 10,000,000; or about 1,000 to about 1,000,000; or about 5,000 to about 500,000; or about 10,000 to about 100,000; or about 20,000 to 50,000.

In some embodiments, the at least one biodegradable polymer comprises poly(lactic-co-glycolic acid) (PLA) or poly(orthoester) (POE) or a combination thereof. The poly (lactic-co-glycolic acid) may comprise a mixture of polyglycolide (PGA) and polylactide and in some embodiments, in the mixture, there is more polylactide than polyglycolide. In various other embodiments there is 100% polylactide and 0% polyglycolide; 95% polylactide and 5% polyglycolide; 90% polylactide and 10% polyglycolide; 85% polylactide and 15% polyglycolide; 80% polylactide and 20% polyglycolide; 75% polylactide and 25% polyglycolide; 70% polylactide and 30% polyglycolide; 65% polylactide and 35% polyglycolide; 60% polylactide and 40% polyglycolide; 55% polylactide and 45% polyglycolide; 50% polylactide and 50% polyglycolide; 45% polylactide and 55% polyglycolide; 40% polylactide and 60% polyglycolide; 35% polylactide and 65% polyglycolide; 30% polylactide and 70% polyglycolide; 25% polylactide and 75% polyglycolide; 20% polylactide and 80% polyglycolide; 15% polylactide and 85% polyglycolide; 10% polylactide and 90% polyglycolide; 5% polylactide and 95% polyglycolide; and 0% polylactide and 100% polyglycolide.

In various embodiments that comprise both polylactide and polyglycolide; there is at least 95% polylactide; at least 90% polylactide; at least 85% polylactide; at least 80% polylactide; at least 75% polylactide; at least 70% polylactide; at least 65% polylactide; at least 60% polylactide; at least 55%; at least 50% polylactide; at least 45% polylactide; at least 40% polylactide; at least 35% polylactide; at least 30% polylactide; at least 25% polylactide; at least 20% polylactide; at least 15% polylactide; at least 10% polylactide; or at least 5% polylactide; and the remainder of the biopolymer being polyglycolide.

In some embodiments, the biodegradable polymer comprises at least 10 wt %, at least 50 wt. %, at least 60 wt. %, at least 70 wt. %, at least 80 wt. %, at least 85 wt. %, at least 90 wt. %, at least 95 wt. %, or at least 99 wt. % of the formulation. In some embodiments, the at least one biodegradable polymer and the analgesic and the anti-inflammatory are the only components of the pharmaceutical formulation.

In some embodiments, at least 75% of the particles have a size from about 1 micrometer to about 250 micrometers. In some embodiments, at least 85% of the particles have a size from about 1 micrometer to about 100 micrometers. In some embodiments, at least 95% of the particles have a size from about 1 micrometer to about 30 micrometers. In some embodiments, all of the particles have a size from about 1 micrometer to about 30 micrometers.

In some embodiments, at least 75% of the particles have a size from about 5 micrometer to about 20 micrometers. In some embodiments, at least 85% of the particles have a size from about 5 micrometers to about 20 micrometers. In some embodiments, at least 95% of the particles have a size from about 5 micrometer to about 20 micrometers. In some embodiments, all of the particles have a size from about 5 micrometer to about 20 micrometers.

The depot may optionally contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfite, sodium bisulfate, sodium thiosulfate, thimerosal, methylparaben, polyvinyl alcohol and phenylethyl alcohol; solubility adjusting agents; stabilizers; and/or cohesion modifiers. Typically, any such inactive materials will be present within the range of 0-75 wt %, and more typically within the range of 0-30 wt %. If the depot is to be placed in the spinal area, in various embodiments, the depot may comprise sterile preservative free material.

The depot can be different sizes, shapes and configurations, such as for example, strip, rod, sheet, mesh, or the like. There are several factors that can be taken into consideration in determining the size, shape and configuration of the drug depot. For example, both the size and shape may allow for ease in positioning the drug depot at the target tissue site that is selected as the implantation site. In addition, the shape and size of the system should be selected so as to minimize or prevent the drug depot from moving after implantation or injection. In various embodiments, the drug depot can be shaped like a pellet, a sphere, a cylinder such as a rod, a flat surface such as a disc, film or sheet, strip, rod, mesh, or the like. Flexibility may be a consideration so as to facilitate placement of the drug depot. In various embodiments, the drug depot can be different sizes, for example, the drug depot may be a length of from about 2 to 4 cm and width of from about 1-2 cm and thickness of from about 0.25 to 1 mm, or length of from about 0.5 mm to 5 cm and have a diameter of from about 0.01 to about 2 mm. In various embodiments, the depot is a strip having dimensions of 2.5 cm×1.5 cm×0.5 mm. In various embodiments, the drug depot may have a layer thickness of from about 0.005 to 1.0 mm, such as, for example, from 0.05 to 0.75 mm.

Anchor

Like the drug depot, the anchor and also the line may be made of biodegradable material. In some embodiments, the anchor and line may degrade slower than the drug depot. For example, the drug depot may degrade in less than 1 month, while the anchor and line may degrade after 3-90 days, 3-10 days, 3-12 days; 3-14 days, 7-10 days, 7-14 days, 7-21 days, 7-30 days, 7-50 days, 7-90 days, 7-140 days, or 14-150 days or after 6 months to 9 months to 1 year. In this way, the drug depot will be held in place at or near the target tissue site by the anchor and line until the drug depot has degraded and released its therapeutic agent. Examples of suitable biodegradable material that the line and/or anchor can be made of include but are not limited to poly(alpha-hydroxy acids), poly(lactide-co-glycolide) (PLGA or PLG), polylactide (PLA), polyglycolide (PG), polyethylene glycol (PEG) conjugates of poly (alpha-hydroxy acids), polyorthoesters, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, poly(glycolide-,-caprolactone), ,-caprolactone, dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof.

Where different combinations of polymers are used (bi, tri (e.g., PLGA-PEO-PLGA) or terpolymers), they may be used in different molar ratios, 1:1, 2:1, 3:1, 4:1, 5:1, 6:1, 7:1, 8:1, 9:1, or 10:1. For example, for a 130-day release drug depot, the polymer make up is 50:50 PLGA to 100 PLA. The molecular weight range is 0.45 to 0.8 dI/g.

In various embodiments, the molecular weight of the polymer can be a wide range of values. The average molecular weight of the polymer can be from about 1000 to about 10,000,000; or about 1,000 to about 1,000,000; or about 5,000 to about 500,000; or about 10,000 to about 100,000; or about 20,000 to 50,000.

In some embodiments, the at least one biodegradable polymer comprises poly(lactic-co-glycolic acid) (PLA) or poly(orthoester) (POE) or a combination thereof. The poly (lactic-co-glycolic acid) may comprise a mixture of polyglycolide (PGA) and polylactide and in some embodiments, in the mixture, there is more polylactide than polyglycolide. In various other embodiments there is 100% polylactide and 0% polyglycolide; 95% polylactide and 5% polyglycolide; 90% polylactide and 10% polyglycolide; 85% polylactide and 15% polyglycolide; 80% polylactide and 20% polyglycolide; 75% polylactide and 25% polyglycolide; 70% polylactide and 30% polyglycolide; 65% polylactide and 35% polyglycolide; 60% polylactide and 40% polyglycolide; 55% polylactide and 45% polyglycolide; 50% polylactide and 50% polyglycolide; 45% polylactide and 55% polyglycolide; 40% polylactide and 60% polyglycolide; 35% polylactide and 65% polyglycolide; 30% polylactide and 70% polyglycolide; 25% polylactide and 75% polyglycolide; 20% polylactide and 80% polyglycolide; 15% polylactide and 85% polyglycolide; 10% polylactide and 90% polyglycolide; 5% polylactide and 95% polyglycolide; and 0% polylactide and 100% polyglycolide.

In various embodiments, the anchor and/or line comprise both polylactide and polyglycolide; there is at least 95% polylactide; at least 90% polylactide; at least 85% polylactide; at least 80% polylactide; at least 75% polylactide; at least 70% polylactide; at least 65% polylactide; at least 60% polylactide; at least 55%; at least 50% polylactide; at least 45% polylactide; at least 40% polylactide; at least 35% polylactide; at least 30% polylactide; at least 25% polylactide; at least 20% polylactide; at least 15% polylactide; at least 10% polylactide; or at least 5% polylactide; and the remainder of the biopolymer being polyglycolide.

The anchor can be different sizes, shapes and configurations, such as for example, strip, pellet, hook, staple, barb, rod, sheet, mesh, or the like. There are several factors that can be taken into consideration in determining the size, shape and configuration of the drug depot. For example, both the size and shape may allow for ease in positioning the anchor at the target tissue site that is selected as the implantation site. In addition, the shape and size of the anchor should be selected so as to minimize or prevent the drug depot from moving after implantation or injection. In various embodiments, the anchor can be shaped like a pellet, hook, staple, barb, a sphere, a cylinder such as a rod, a flat surface such as a disc, film or sheet, strip, rod, mesh, or the like. Flexibility may be a consideration so as to facilitate placement of the drug depot. In various embodiments, the anchor can be different sizes, for example, the anchor may be a length of from about 2 to 4 cm and width of from about 1-2 cm and thickness of from about 0.25 to 1 mm, or length of from about 0.5 mm to 5 cm and have a diameter of from about 0.01 to about 2 mm, or from 0.2 mm to about 1 mm, or from 0.7 to about 0.8 mm in diameter.

In various embodiments, the anchor comprises wings that when delivered from the cannula or needle, expand to catch tissue and hold the drug depot in position at or near the target tissue site.

Cannula or Needle

The drug depot, anchor and/or line can be loaded in a cannula or needle that is designed to cause minimal physical and psychological trauma to the patient. Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. The cannula or needle may optionally include one or more tapered regions. In various embodiments, the cannula or needle may be beveled. The cannula or needle may also have a tip style vital for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks.

The cannula or needle of the drug depot device has a diameter that is larger than the diameter of at least part of the plunger (e.g., tip, middle, etc.) to allow at least part of the plunger to be slidably received within the cannula or needle. In various embodiments, the diameter of the cannula or needle is substantially the same throughout. In other embodiments, the diameter of the needle or cannula becomes smaller approaching the distal end for drug delivery.

The dimensions of the hollow cannula or needle, among other things, will depend on the site for implantation. For example, the width of the epidural space is only about 3-5 mm for the thoracic region and about 5-7 mm for the lumbar region. Thus, the needle or cannula, in various embodiments, can be designed for these specific areas. Some examples of lengths of the cannula or needle may include, but are not limited to, from about 50 to 150 mm in length, for example, about 65 mm for epidural pediatric use, about 85 mm for a standard adult and about 150 mm for an obese adult patient. The thickness of the cannula or needle will also depend on the site of implantation. In various embodiments, the thickness includes, but is not limited to, from about 0.05 to about 1.655. The gauge of the cannula or needle may be the widest or smallest diameter or a diameter in between for insertion into a human or animal body. The widest diameter is typically about 14 gauge, while the smallest diameter is about 25 gauge. In various embodiments the gauge of the needle or cannula is about 17 to about 25 gauge.

In various embodiments, the plunger, cannula and/or drug depot include markings that indicate location at or near the site beneath the skin. Radiographic markers can be included on the drug depot to permit the user to accurately position the depot into the site of the patient. These radiographic markers will also permit the user to track movement and degradation of the depot at the site over time. In this embodiment, the user may accurately position the depot in the site using any of the numerous diagnostic-imaging procedures. Such diagnostic imaging procedures include, for example, X-ray imaging or fluoroscopy. Examples of such radiographic markers include, but are not limited to, barium, calcium phosphate, and/or metal beads.

In various embodiments, the needle or cannula may include a transparent or translucent portion that can be visualizable by ultrasound, fluoroscopy, x-ray, or other imaging techniques. In such embodiments, the transparent or translucent portion may include a radiopaque material or ultrasound responsive topography that increases the contrast of the needle or cannula relative to the absence of the material or topography.

In various embodiments, a drug depot implantable at or near a target tissue site beneath the skin of a patient is provided, the drug depot comprising a therapeutically effective amount of a drug; at least one line having a distal end and a proximal end, the proximal end of the line attached to the drug depot; an anchor attached to the distal end of the line and configured to limit movement of the drug depot at or near the target tissue site, wherein the drug depot is capable of releasing the therapeutically effective amount of the drug over a period of at least one day.

Figure 1B:
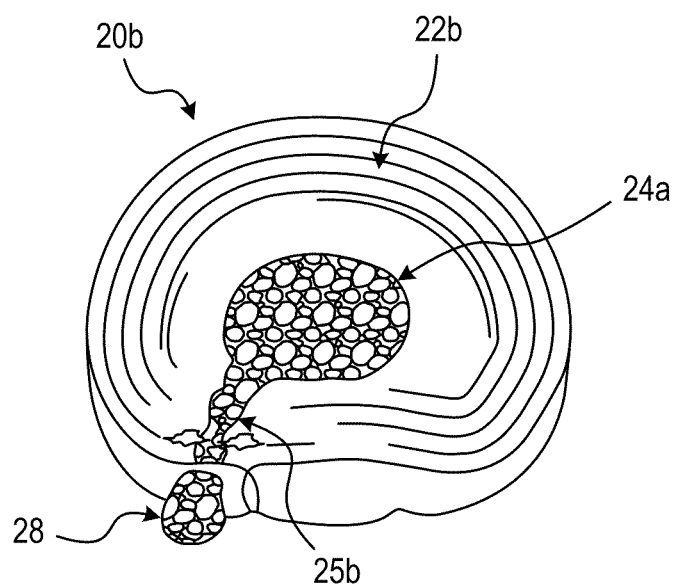
FIG. 1B is a cross-sectional view of a target tissue site, which is a herniated intervertebral disc where the disc has ruptured.

For purposes of illustration only, FIG. 1A illustrates an example of a target tissue site, which is shown as an intervertebral disc 20a. The intervertebral disc 20a is made up of two components: the annulus fibrosus 22a and the nucleus pulposus 24a. The nucleus pulposus 24a is the inner gelatinous material surrounded by the annulus fibrosus. It distributes mechanical loads placed upon the disc 20a, while the annulus fibrosus 22a provides structural integrity and constrains the nucleus pulposus 24a to a specific spinal region. The annulus fibrosus 22a is designed with fibrocartilaginous and fibrous tissue arranged in concentric layers called laminae. As one moves, from the nucleus pulposus to the periphery, the annulus fibrosus tissue becomes more dense, stronger, less elastic, less fluid, and more ligamentous until reaching the outermost layers. There, the tissue actually becomes a tough, capsular ligament. The annulus fibrosus 22a can become weaker with age, and may begin to tear. As shown in FIG. 1A, defects in the annulus fibrosus called annular tears, 22a allow bulging 26 of the nucleus pulposus in the early stages. As time progresses, as shown in FIG. 1B, it often leads to a complete rupturing 28 of the annulus fibrosus 22a and 22b. The herniated 20a or ruptured 20b disc compresses the spinal canal and exerts pressure on the nerve roots that pass through the disc 20a, 20b causing lower back pain. In addition, the nucleus pulposus 24a contains significant amounts of substances capable of exciting, or increasing the excitability of, sensory nerves such as prostaglandin E, histamine-like substances, lactic acid and polypeptide amines. These substances may escape through the annular tears 28, increasing the lower back pain or resulting in radiating leg pain. In addition, the annular tears 25a and 25b cause fibrous tissue to grow in the tear, which increases pain and/or inflammation.

Because this target tissue site is a difficult site to place a drug depot without it migrating away, by employing an anchor that tethers the drug depot just outside the annular tear, pain and/or inflammation is reduced, inhibited and/or eliminated.

Figure 2:
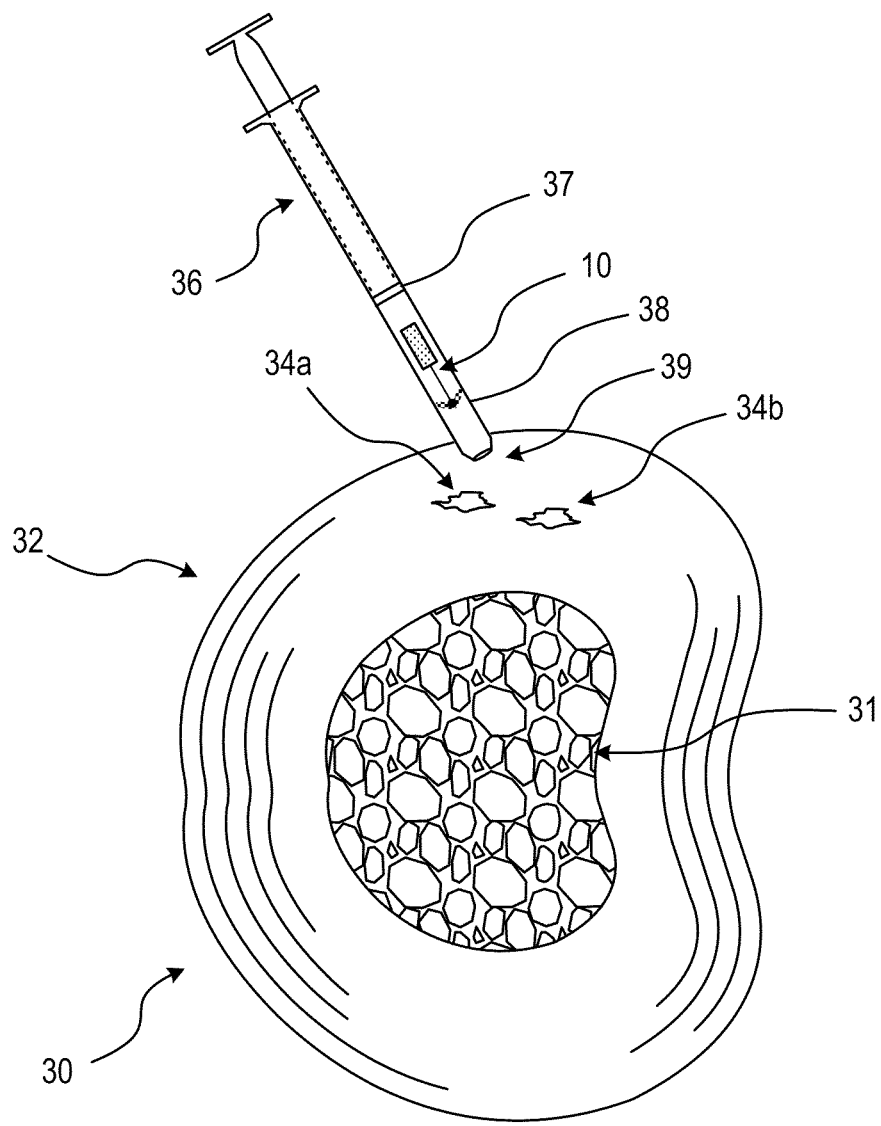
FIG. 2 is a cross-sectional view illustrating one embodiment of the implantable drug depot having an anchor attached to the drug depot by a line (e.g., suture, yarn, etc.) that is being administered into an intervertebral disc having an annulus.

FIG. 2 illustrates an intervertebral disc 30 having annular tears 34a and 34b in annulus fibrosis 32. However, this intervertebral disc is not ruptured, as the nucleus pulposus 31 is contained at this stage. The drug depot 10 is delivered (via a syringe 36 through a needle 38 using plunger 37) into tissue adjacent to tears 34a and 34b. The drug depot and anchor may be injected into the tissue within about 1 cm, 2 cm, or 5 cm of the defect, where the anchor will catch the adjacent tissue 39 and the depot will be tethered outside the annular tears 34a and 34b. In this way, migration of the drug depot from the site will be reduced and/or eliminated and target directed delivery of the drug can be accomplished.

Figure 3:
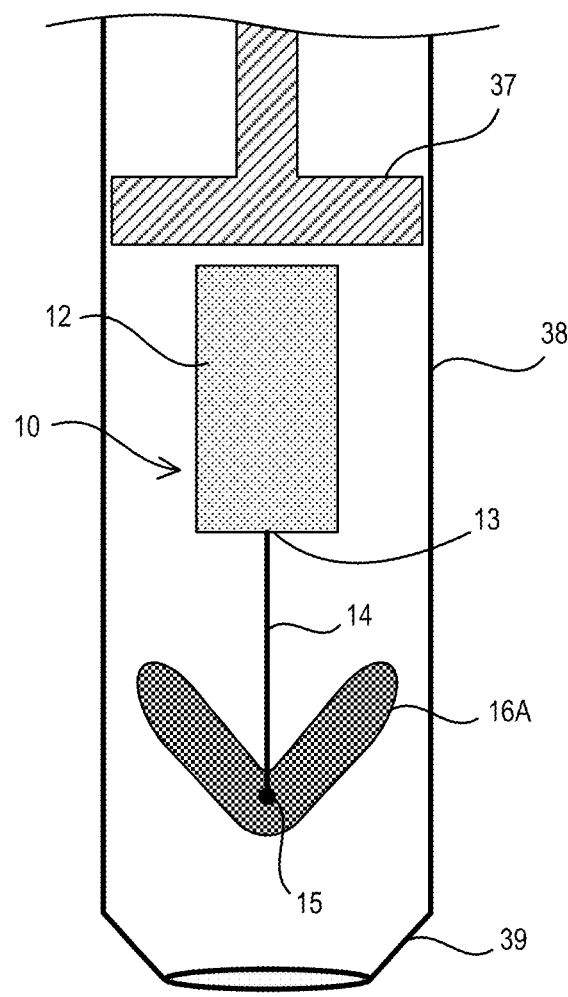
FIG. 3 is a magnified side sectional view of one embodiment of the implantable drug depot having a winged anchor attached to it by a suture. In this embodiment, the drug depot is loaded in a cannula or needle and the wings are retracted.

FIG. 3 is a magnified side sectional view of one embodiment of the implantable drug depot 10 loaded in cannula or needle 38, which can be deployed by pushing plunger 37 and the depot will be directed out the distal end 39 of the cannula or needle. The implantable drug depot comprises the drug depot 12 with a line 14 (e.g., suture, yarn, thread, and/or wire). The proximal end of the line 13 is attached to the distal end of the drug depot. The line can be made pre-attached to the drug depot and/or anchor as one unit. Alternatively, the line can be attached to the drug depot as a knot, rim, bead or clip or the drug depot and/or anchor may have a port, groove, slit, loop, hook, barb, post, channel, and/or clip for the line to be attached thereto. The line can be attached to the center point of the drug depot or off center. The line can space the drug depot from the anchor by a distance of from about 0.1 mm, 1 mm, 2 mm, 5 mm to about 1 cm, 2 cm, 5 cm. Of course the spacing and distance the anchor is from the depot and the length of the line will depend on the target tissue site. For example, implant sites at or near the spine will often be in the 0.5 mm to 2 mm range.

In some embodiments, the anchor can be embedded inside the disc about 1 cm in from the perimeter of the disc's outer surface, and the drug depot will be about 1 mm from the anchor if desired to keep depot inside the annular tear, or about the drug depot may be, in some embodiments, hanging out of the disc about 0.1 mm to 10 mm from the disc surface.

The distal end of the line 15 can be attached to the anchor 16A at a point in the center or off center. In the illustrated embodiment, the anchor 16A is a winged anchor that is in a retracted or contracted position within the cannula or needle. When deployed, the anchor will expand and the wings will catch the tissue plane as the cannula or needle is retracted.

Figure 4:
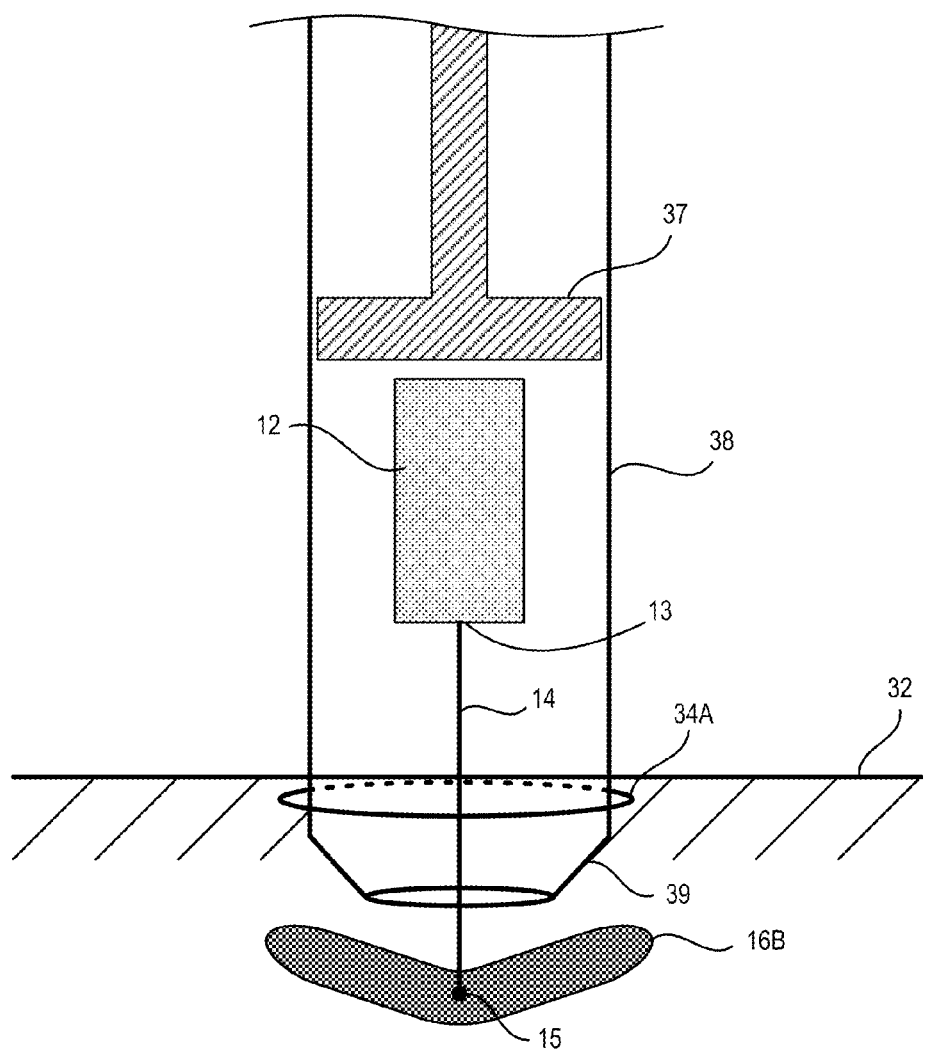
FIG. 4 is a magnified side sectional view of one embodiment of the implantable drug depot having a winged anchor attached to it by a suture. In this embodiment, the anchor is being delivered in an annular tear and as the cannula or needle is being withdrawn, the winged anchor expands and catches the tissue plane to hold the drug depot in a position outside of the annular tear.

FIG. 4 is a magnified side sectional view of one embodiment of the implantable drug depot 10 being deployed from the cannula or needle 38 by pushing plunger 37, where the depot is directed out the distal end 39 of the cannula or needle. The implantable drug depot comprises the drug depot 12 with a line 14 (e.g., suture, yarn, thread, and/or wire). The proximal end of the line 13 is attached to the distal end of the drug depot. The distal end of the line 15 can be attached to the anchor 16B at a point in the center or off center. In the illustrated embodiment, the anchor 16B is a winged anchor that is in an expanded or open position inside an annular tear 34a. Thus, the anchor catches the tissue plane of the intervertebral disc 32 as the cannula or needle is retracted. The drug depot will now be tethered at the site of pain and/or inflammation outside the annular tear where often fibrous tissue and blood vessels begin to proliferate causing pain and/or inflammation. The drug depot will be at or near this site and a therapeutic agent (e.g., anti-inflammatory agent, analgesic, etc.) can be released over time as the drug depot degrades. Often the anchor and line will degrade slower than the drug depot. In this way, the drug will be released and the depot depleted or substantially depleted before the suture and anchor will degrade.

Figure 5:
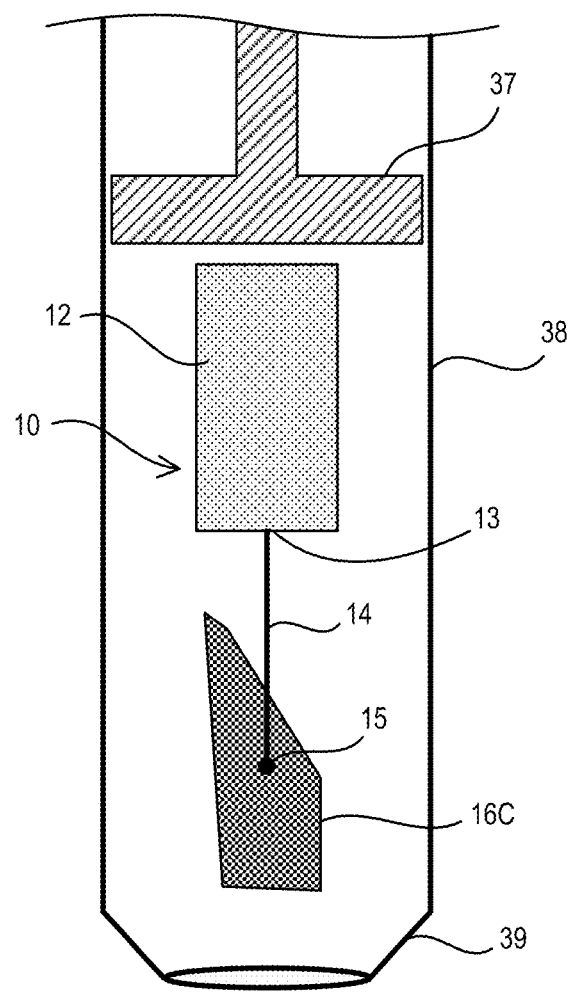
FIG. 5 is a magnified side sectional view of one embodiment of the implantable drug depot having an anchor attached to it by a suture. In this embodiment, the drug depot is loaded in a cannula or needle and the anchor is capable of rotating clockwise or counterclockwise to catch the tissue plane and hold the drug depot in position at or near the target tissue site (e.g., annular tear).

FIG. 5 is a magnified side sectional view of one embodiment of the implantable drug depot 10 loaded in cannula or needle 38, which can be deployed by pushing plunger 37 and the depot will be directed out the distal end 39 of the cannula or needle. The implantable drug depot comprises the drug depot 12 with a line 14 (e.g., suture, yarn, thread, and/or wire). The proximal end of the line 13 is attached to the distal end of the drug depot. In turn, the distal end of the line 15 is attached to the anchor 16C at a point off center with respect to the depot. In the illustrated embodiment, when the cannula or needle is withdrawn, the anchor will be turned clockwise or counterclockwise to catch the tissue plane as the cannula or needle is retracted.

Figure 6:
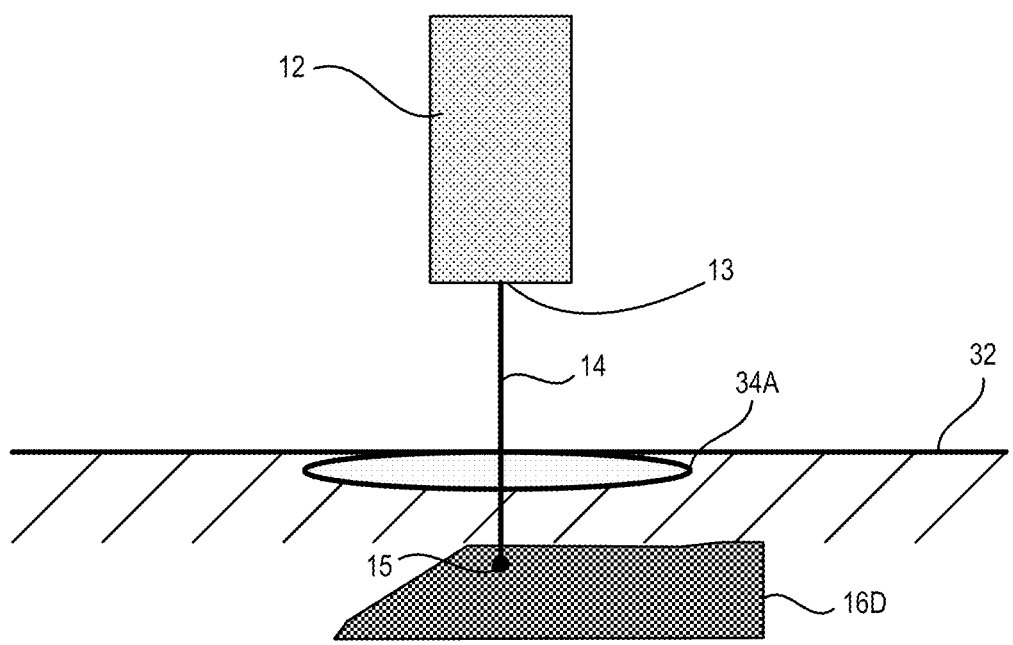
FIG. 6 is a magnified side sectional view of one embodiment of the implantable drug depot having an anchor attached to it by a suture. In this embodiment, the anchor was delivered in an annular tear and as the cannula or needle was withdrawn, the anchor was rotated clockwise or counterclockwise to catch the tissue and hold the drug depot in position outside of the annular tear.

FIG. 6 is a magnified side sectional view of one embodiment of the implantable drug depot 10 being deployed from the cannula or needle 38. By pushing plunger 37, the depot is directed out the distal end 39 of the cannula or needle. The implantable drug depot comprises the drug depot 12 with a line 14 (e.g., suture, yarn, thread, and/or wire). The proximal end 13 of the line is attached to the distal end of the drug depot. The distal end of the line 15 can be attached to the anchor 16D at a point off center. In the illustrated embodiment, when the cannula or needle was withdrawn, the anchor was turned clockwise or counterclockwise as a result of friction from the line being pulled. The anchor then caught the tissue plane as the cannula or needle was retracted. The drug depot will now be tethered at the site of pain and/or inflammation outside the annular tear where often fibrous tissue and blood vessels begin to proliferate. The drug depot is illustrated at or near this site and a therapeutic agent (e.g., anti-inflammatory agent, analgesic, etc.) can be released over time as the drug depot degrades.

In various embodiments, the drug depot, anchor, and line allow the drug depot to stay at difficult areas particularly areas with little or no tissue. For example, in the spinal area, there is little or no tissue surrounding the intervertebral disc. The areas surrounding the disc comprise mostly CSF and other fluid. Thus, keeping a drug depot at the spinal site may be difficult. Utilizing the anchor, the drug depot will be held in position in the fluid area where the therapeutic agent can exert its effect. It will be understood by those of ordinary skill in the art that the drug depot and anchor can be delivered to any site beneath the skin, including, but not limited to, at least one muscle, ligament, tendon, cartilage, spinal disc, spinal for aminal space, near the spinal nerve root, or spinal canal.

Although the drug depot and/or anchor are shown in the figures as rectangular shapes. It will be understood by one or ordinary skill in the art that the drug depot and/or anchor can be any shape (e.g., pellet, oval, strip, rod, sheet, mesh, or the like). It will also be understood by one of ordinary skill in the art that the attachment surface of the drug depot and/or anchor can include one or more ports, grooves, slits, loops, hooks, barbs, posts, channels and/or clips adapted to receive the one or more lines.

It will be understood by those of ordinary skill in the art that the one or more channels, grooves, slits, loops, hooks, barbs, posts and/or clips can be made of the same or different material than the drug depot. It will also be understood by those of ordinary skill in the art that the one or more lines (e.g., suture, yarn, thread, and/or wire etc.) can be made of the same or different material as the drug depot and/or anchor.

In some embodiments, the holes, channels, grooves, slits, or the like can be made by punching, drilling, laser, or the like. In some embodiments, the suture can be attached by hand or machine to the drug depot. Suture knots can be created by hand or automated machine. Other capture means or mechanisms (channels, holes, ports, grooves, slits, loops, hooks, barbs, posts, beads, tabs, and/or clips) can be pre-molded into depot implant shape, machined in, or attached secondarily.

Radiographic markers can be included on the drug depot to permit the user to position the depot accurately into the target site of the patient. These radiographic markers will also permit the user to track movement and degradation of the depot at the site over time. In this embodiment, the user may accurately position the depot in the site using any of the numerous diagnostic imaging procedures. Such diagnostic imaging procedures include, for example, X-ray imaging, fluoroscopy, or MRI. Examples of such radiographic markers include, but are not limited to, barium, calcium phosphate, and/or metal beads or particles. In various embodiments, the radiographic marker could be a spherical shape, a line(s), or a ring around the depot.

In some embodiments, the drug depot may have an initial burst effect to release the drug shortly after it is implanted. Various factors can be adjusted to achieve the initial burst of therapeutic agent release. First, the initial burst can be controlled by factors related to the property of the depot, such as the water immiscibility of the solvent, polymer/solvent ratio, and the property of the polymer. The extent of water immiscibility of the solvent used in the depot affects that rate aqueous body fluid can penetrate the depot to release the therapeutic agent. Generally, higher water solubility leads to a higher initial burst while water immiscibility leads to a lower initial burst or slower release (sustained release) of the therapeutic agent.

Suitable solvents that can be used to control initial burst release or sustained release include, but are not limited to, methyl benzoate, ethyl benzoate, n-propyl benzoate, isopropyl benzoate, butyl benzoate, isobutyl benzoate, sec-butyl benzoate, tert-butyl benzoate, isoamyl benzoate, benzyl benzoate, water, alcohol, low molecular weight PEG (less than 1,000 MW), triacetin, diacetin, tributyrin, triethyl citrate, tributyl citrate, acetyl triethyl citrate, acetyl tributyl citrate, triethylglycerides, triethyl phosphate, diethyl phthalate, diethyl tartrate, mineral oil, polybutene, silicone fluid, glycerin, ethylene glycol, octanol, ethyl lactate, propylene glycol, propylene carbonate, ethylene carbonate, butyrolactone, ethylene oxide, propylene oxide, N-methyl-2-pyrrolidone, 2-pyrrolidone, glycerol formal, methyl acetate, ethyl acetate, methyl ethyl ketone, dimethylformamide, glycofurol, dimethyl sulfoxide, tetrahydrofuran, caprolactam, decylmethylsulfoxide, oleic acid, 1-dodecylazacyclo-heptan-2-one, or mixtures thereof. The solvent can be mixed, in various embodiments, with the therapeutic agent and/or polymers to obtain the desired release profile.

The depot may have pore forming agents, which include biocompatible materials that when contacted with body fluids dissolve, disperse or degrade to create pores or channels in the polymer matrix. Typically, organic and non-organic materials that are water soluble such as sugars (e.g., sucrose, dextrose), water soluble salts (e.g., sodium chloride, sodium phosphate, potassium chloride, and sodium carbonate), water soluble solvents such as N-methyl-2-pyrrolidone and polyethylene glycol and water soluble polymers (e.g., carboxymethylcellulose, hydroxypropyl-cellulose, and the like) can conveniently be used as pore formers. Such materials may be present in amounts varying from about 0.1% to about 100% of the weight of the polymer, but will typically be less than 50% and more typically less than 10-20% of the weight of polymer.

Further, varying the molecular weight of the polymer in the depot, or adjusting the molecular weight distribution of the polymer material in the depot vehicle can affect the initial burst and the release rate of therapeutic agent from the depot. Generally, a higher molecular weight polymer renders a lower initial burst and slower release rate of the therapeutic agent. The polymers may have different end groups such as acid and ester end groups. As persons of ordinary skill in the art are aware, implantable elastomeric depot compositions having a blend of polymers with different end groups are used the resulting formulation will have a lower burst index and a regulated duration of delivery. For example, one may use polymers with acid (e.g., carboxylic acid) and ester end groups (e.g., methyl of ethyl ester end groups).

Additionally, by varying the comonomer ratio of the various monomers that form a polymer (e.g., the L/G (lactic acid/glycolic acid) or G/CL (glycolic acid/polycaprolactone) ratio for a given polymer) there will be a resulting depot composition having a regulated burst index and duration of delivery. For example, a depot composition having a polymer with a L/G ratio of 50:50 may have a short duration of delivery ranging from about two days to about one month; a depot composition having a polymer with a L/G ratio of 65:35 may have a duration of delivery of about two months; a depot composition having a polymer with a L/G ratio of 75:25 or L/CL ratio of 75:25 may have a duration of delivery of about three months to about four months; a depot composition having a polymer ratio with a L/G ratio of 85:15 may have a duration of delivery of about five months; a depot composition having a polymer with a L/CL ratio of 25:75 or PLA may have a duration of delivery greater than or equal to six months; a depot composition having a terpolymer of CL/G/L with G greater than 50% and L greater than 10% may have a duration of delivery of about one month and a depot composition having a terpolymer of CL/G/L with G less than 50% and L less than 10% may have a duration months up to six months. In general, increasing the G content relative to the CL content shortens the duration of delivery whereas increasing the CL content relative to the G content lengthens the duration of delivery. Thus, among other things, depot compositions having a blend of polymers having different molecular weights, end groups and comonomer ratios can be used to create a depot formulation having a lower burst index and a regulated duration of delivery.

Factors such as the particle size, the disintegration of the particulates, the morphology of the particulates (e.g., whether pores are present in the particulates before implanting or can be formed easily by body fluid attack), coatings, complex formation by the therapeutic agent and the strength of complex bond, can be manipulated to achieve the desired low initial burst and release rate.

Line

The line may be resorbable or permanent in nature depending upon the type of material from which it is made. The line may comprise a suture, yarn, thread, and/or wire.

As used herein, "suture" refers to any flexible structure that can be stretched between two points and includes, without limitation, traditional suture material, single or multiple stranded threads, or a mesh structure. A suture may also be a strap-like structure with a number of holes in it, similar to the holes found in a belt. A "suture" may also take the form of an acellular, collagen membrane or other biologic tissue augment, which may provide a scaffold or support matrix for cellular ingrowth to allow soft tissue to reconstruct itself. Sutures may include silk, nylon, linen, cotton, chromic gut, plain gut, cat gut, vicryl, polyglactin, polyester, polypropylene, stainless steel, synthetic polymers having glycolic acid ester linkages subject to hydrolytic degradation to non-toxic tissue compatible absorbable components, including polyglycolic acid. The suture may be monofilamentary or braided, absorbable or non-absorbable. The suture may be of any length. In various embodiments, the suture is long enough to reach from the site of placement of the depot to the target tissue site. The suture may be of any thickness provided it can be attached to or pass through the drug depot and/or anchor. In some embodiments, the suture may be coated with a drug.

A variety of bioabsorbable polymers can be used to make the suture. Examples of suitable biocompatible, bioabsorbable polymers include aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, biomolecules (i.e., biopolymers such as collagen, elastin, bioabsorbable starches, etc.) or blends thereof. Polyesters include, but are not limited to, homopolymers and copolymers of lactide (which includes lactic acid, D-,L- and meso lactide), glycolide (including glycolic acid), caprolactone, p-dioxanone (1,4-dioxan-2-one), trimethylene carbonate (1,3-dioxan-2-one), alkyl derivatives of trimethylene carbonate, delta-valerolactone, beta-butyrolactone, gamma-butyrolactone, epsilon-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one 2,5-diketomorpholine, pivalolactone, alpha-diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one or polymer blends thereof.

In some embodiments, the suture can comprise shape memory polymers including various polyethers, polyacrylates, polyamides, polysiloxanes, polyurethanes, polyether amides, polyurethane/ureas, polyether esters, or urethanelbutadiene copolymers or a combination thereof.

In some embodiments, the suture degrades slower than the drug depot. Sutures may be of different sizes depending on the procedure being performed and the implant site. Sutures can range in size from #000000 (#6-0 or #6/0), #00 (#2-0 or #2/0), #0, #1, #2, #3, #4, #5, #6, with #000000 being the smallest. In various embodiments, the drug depot and/or suture will have one or more channels, grooves, slits, loops, hooks, and/or barbs that will be larger than #000000, #00, #0, #1, #2, #3, #4, #5, or #6, range so that the suture can pass through the surface of the drug depot.

Sterilization

The drug depot, anchor, line, and/or medical device to administer the drug, may be sterilizable. In various embodiments, one or more components of the drug depot, medical device to administer the drug, line (e.g., suture) and/or anchor may be sterilizable by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In some embodiments, the drug depot, anchor, line and/or needle is pre-assembled, packaged in a moisture resistant package and then terminally sterilized by gamma irradiation. In use the surgeon removes the pre-assembled drug depot from the sterile package for use.

In various embodiments, electron beam (e-beam) radiation may be used to sterilize one or more components of the device (e.g., drug depot, anchor, line, needle, etc.). E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize the depot and/or one or more components of the device, including, but not limited to, gas sterilization, such as, for example, with ethylene oxide or steam sterilization.

Kits

In various embodiments, a kit is provided comprising one or more drug depots, line, and anchoring member. The kit may include additional parts along with the drug depot and/or medical device combined together to be used to implant the drug depots (e.g., pellets, strips, meshes etc.). The kit may include the drug depot delivery device in a first compartment. The second compartment may include a canister holding the drug depots and any other instruments needed for the localized drug delivery. A third compartment may include gloves, drapes, needles, wound dressings and other procedural supplies for maintaining sterility of the implanting process, as well as an instruction booklet. A fourth compartment may include additional needles and/or sutures. Each tool may be separately packaged in a plastic pouch that is radiation sterilized. A fifth compartment may include an agent for radiographic imaging. A cover of the kit may include illustrations of the implanting procedure and a clear plastic cover may be placed over the compartments to maintain sterility.

Administration

In various embodiments, the drug depot may be parenterally administered. The term "parenteral" as used herein refers to modes of administration, which bypass the gastrointestinal tract, and include for example, intramuscular, intraperitoneal, intrasternal, subcutaneous, intra-operatively, intrathecally, intradiskally, peridiskally, epidurally, perispinally, intraarticular or combinations thereof.

In various embodiments, because the combination of analgesic and/or anti-inflammatory agent is locally administered, therapeutically effective doses may be less than doses administered by other routes (oral, topical, etc.). In turn, systemic side effects, such as, for example, liver transaminase elevations, hepatitis, liver failure, myopathy, constipation, etc. may be reduced or eliminated.

The drug depot can be delivered to any site beneath the skin, including, but not limited to, at least one muscle, ligament, tendon, cartilage, spinal disc, spinal foraminal space, near the spinal nerve root, or spinal canal.

In various embodiments, a method is provided for treating or preventing pain or inflammation in a patient in need of such treatment, the method comprising implanting one or more biodegradable drug depots comprising a therapeutically effective amount of an analgesic and/or anti-inflammatory agent at or near a target tissue site beneath the skin, wherein the one or more drug depots comprise at least one biodegradable suture having a distal end and a proximal end, the proximal end of the at least one suture attached to the one or more drug depots; a biodegradable anchoring pellet attached to the distal end of the at least one suture and configured to limit movement of the one or more drug depots at or near the target tissue site, wherein the drug depot is capable of releasing the therapeutically effective amount of the drug over a period of at least three days.

In various embodiments, a method is provided for treating or preventing pain or inflammation in a patient in need of such treatment, the method comprising implanting one or more biodegradable drug depots comprising a therapeutically effective amount of an analgesic and/or anti-inflammatory agent at or near a target tissue site beneath the skin, wherein the one or more drug depots comprise at least one biodegradable suture having a distal end and a proximal end, the proximal end of the at least one suture attached to the one or more drug depots; a biodegradable anchoring pellet attached to the distal end of the at least one suture and configured to limit movement of the one or more drug depots at or near the target tissue site, wherein the drug depot is capable of releasing the therapeutically effective amount of the drug over a period of at least three days.

Another embodiment provides a method for treating a mammal suffering from inflammation and/or pain, said method comprising administering a therapeutically effective amount of at least one analgesic agent and at least one anti-inflammatory agent at a target site beneath the skin at or near the target site. The at least one analgesic agent and at least one anti-inflammatory agent may for example be administered locally to the target tissue site as a drug depot.

In some embodiments, the therapeutically effective dosage amount and the release rate profile are sufficient to reduce inflammation and/or pain for a period of at least one day, for example, 1-90 days, 1-10 days, 1-3 days, 3-7 days, 3-12 days; 3-14 days, 7-10 days, 7-14 days, 7-21 days, 7-30 days, 7-50 days, 7-90 days, 7-140 days, or 14-140 days.

In some embodiments the at least one analgesic agent and at least one anti-inflammatory agent or a portion of the at least one analgesic agent and at least one anti-inflammatory agent are administered as a bolus dose at the target tissue to provide an immediate release of the at least one analgesic agent and at least one anti-inflammatory agent.

In some embodiments there is a composition useful for the treatment of inflammation comprising an effective amount of at least one analgesic agent and at least one anti-inflammatory agent that is capable of being administered to e.g., a pain or inflammatory site. By way of example, they may be administered locally to the foraminal spine, paraspinal muscles or subcutaneous tissues.

In some embodiments, the at least one analgesic agent and/or at least one anti-inflammatory agent are administered by placement of the drug depot into an open patient cavity during surgery. In some embodiments, the drug depot can be placed at postions around the pain generator using a strategy of triangulation.

A strategy of triangulation may be effective when administering multiple depot pharmaceutical formulations. Thus, a plurality (at least two, at least three, at least four, at least five, at least six, at least seven, etc.) drug depots comprising the pharmaceutical formulations may be placed around the target tissue site (also known as the pain generator or pain generation site) such that the target tissue site falls within a region that is either between the formulations when there are two, or within an area whose perimeter is defined by a set of plurality of formulations.

In some embodiments, the drug depot is implantable at or near a target tissue site at the time of surgery. The active ingredients may then be released from the depot via diffusion in a sustained fashion over a period of time, e.g., 1-3 days, 3-15 days, 5-10 days or 7-10 days post surgery in order to address pain and inflammation.

In some embodiments, a desired release profile is maintained for at least three days, at least ten days, at least twenty days, at least thirty days, at least forty days, at least fifty days, at least ninety days, at least one hundred days, at least one-hundred and thirty-five days, or at least one-hundred and fifty days, or at least one hundred and eighty days.

In some embodiments, the drug depot may release 5%, 10%, 15%, 20%, 25%, 30%, 40%, 50%, 60%, 70%, 80%, 90%, 95%, or 99% of the at least one analgesic agent or pharmaceutically acceptable salt thereof and at least one anti-inflammatory agent or pharmaceutically acceptable salt thereof relative to a total amount of at least one analgesic agent or pharmaceutically acceptable salt thereof and at least one anti-inflammatory agent loaded in the drug depot over a period of at least three days, at least seven days, at least ten days, at least twenty days, at least thirty days, at least forty days, at least fifty days, at least ninety days, at least one hundred days, at least one-hundred and thirty-five days, at least one-hundred and fifty days, or at least one hundred and eighty days. In various embodiments, the analgesic will be released in an initial burst dose, then the analgesic will be released daily for 3 days and then stop (e.g., this will be suitable to reduce, prevent or treat, post-operative pain), while the anti-inflammatory agent will be released daily without a burst dose for 3 to 12 days, 5 to 10 days or 7 to 10 days after the drug depot is administered to the target tissue site.

In various embodiments, an implantable drug depot useful for reducing, preventing or treating pain and inflammation is provided in a patient in need of such treatment, the implantable drug depot comprising a therapeutically effective amount of an analgesic and/or an anti-inflammatory agent or pharmaceutically acceptable salts thereof, the depot being implantable at a site beneath the skin to reduce, prevent or treat pain and/or inflammation, wherein the drug depot (i) comprises one or more immediate release layer(s) that is capable of releasing about 5% to about 20% of the analgesic and the anti-inflammatory agent or pharmaceutically acceptable salts thereof relative to a total amount of the analgesic and the anti-inflammatory agent or pharmaceutically acceptable salts thereof loaded in the drug depot over a first period of up to 48 hours and (ii) one or more sustain release layer(s) that is capable of releasing about 21% to about 99% of the analgesic and the anti-inflammatory agent or pharmaceutically acceptable salts thereof relative to a total amount of the analgesic and/or the anti-inflammatory agent or pharmaceutically acceptable salts thereof loaded in the drug depot over a subsequent period of up to 3 days to 6 months or 3 days to 2 weeks.

By way of non-limiting example, the target tissue site may comprise at least one muscle, ligament, tendon, cartilage, spinal disc, spinal foraminal space near the spinal nerve root, facet or spinal canal. The target tissue may be associated with an acute disease or chronic disease or surgery.

In some embodiments, an implantable drug depot is provided, wherein the drug depot (i) comprises one or more immediate release layer(s) that releases a bolus dose of at least one analgesic agent or pharmaceutically acceptable salt thereof and at least one anti-inflammatory agent or pharmaceutically acceptable salt thereof at a site beneath the skin and (ii) one or more sustain release layer(s) that releases an effective amount of at least one analgesic agent or pharmaceutically acceptable salt thereof and at least one anti-inflammatory agent or pharmaceutically acceptable salt thereof over a period of 3 days to 6 months. By way of example, in the drug depot, the one or more immediate release layer(s) may comprise poly(lactide-co-glycolide) (PLGA) and the one or more sustain release layer(s) may comprise polylactide (PLA).

In some embodiments, a method is provided of treating or preventing pain or inflammation in a patient in need of such treatment, the method comprising implanting at or near the target tissue site one or more biodegradable drug depots comprising a therapeutically effective amount of an analgesic and/or anti-inflammatory agent at or near a target tissue site beneath the skin, wherein the one or more drug depots comprise at least one biodegradable suture having a distal end and a proximal end, the proximal end of the at least one suture attached to the one or more drug depots; a biodegradable anchoring pellet attached to the distal end of the at least one suture and configured to limit movement of the one or more drug depots at or near the target tissue site, wherein the anchoring pellet is turned clockwise or counterclockwise when implanted so as to lodge the anchoring pellet at or near the target tissue site or the anchoring pellet comprises a plurality of wings that open on delivery and lodge the anchoring pellet at or near the target tissue site.

Method of Making

In various embodiments, the drug depot comprising the active ingredients can be made by combining a biocompatible polymer and a therapeutically effective amount of the active ingredients or pharmaceutically acceptable salts thereof and forming the implantable drug depot from the combination.

Where solution processing techniques are used, a solvent system is typically selected that contains one or more solvent species. The solvent system is generally a good solvent for at least one component of interest, for example, biocompatible polymer and/or therapeutic agent. The particular solvent species that make up the solvent system can also be selected based on other characteristics, including drying rate and surface tension.

Solution processing techniques include solvent casting techniques, spin coating techniques, web coating techniques, solvent spraying techniques, dipping techniques, techniques involving coating via mechanical suspension, including air suspension (e.g., fluidized coating), ink jet techniques and electrostatic techniques. Where appropriate, techniques such as those listed above can be repeated or combined to build up the depot to obtain the desired release rate and desired thickness.

In various embodiments, a solution containing solvent and biocompatible polymer are combined and placed in a mold of the desired size and shape. In this way, polymeric regions, including barrier layers, lubricious layers, and so forth can be formed. If desired, the solution can further comprise, one or more of the following: other therapeutic agent(s) and other optional additives such as radiographic agent(s), etc. in dissolved or dispersed form. This results in a polymeric matrix region containing these species after solvent removal. In other embodiments, a solution containing solvent with dissolved or dispersed therapeutic agent is applied to a pre-existing polymeric region, which can be formed using a variety of techniques including solution processing and thermoplastic processing techniques, whereupon the therapeutic agent is imbibed into the polymeric region.

Thermoplastic processing techniques for forming the depot or portions thereof include molding techniques (for example, injection molding, rotational molding, and so forth), extrusion techniques (for example, extrusion, co-extrusion, multi-layer extrusion, and so forth) and casting.

Thermoplastic processing in accordance with various embodiments comprises mixing or compounding, in one or more stages, the biocompatible polymer(s) and one or more of the following: the active ingredients, optional additional therapeutic agent(s), radiographic agent(s), and so forth. The resulting mixture is then shaped into an implantable drug depot. The mixing and shaping operations may be performed using any of the conventional devices known in the art for such purposes.

During thermoplastic processing, there exists the potential for the therapeutic agent(s) to degrade, for example, due to elevated temperatures and/or mechanical shear that are associated with such processing. For example, certain therapeutic agents may undergo substantial degradation under ordinary thermoplastic processing conditions. Hence, processing is preferably performed under modified conditions, which prevent the substantial degradation of the therapeutic agent(s). Although it is understood that some degradation may be unavoidable during thermoplastic processing, degradation is generally limited to 10% or less. Among the processing conditions that may be controlled during processing to avoid substantial degradation of the therapeutic agent(s) are temperature, applied shear rate, applied shear stress, residence time of the mixture containing the therapeutic agent, and the technique by which the polymeric material and the therapeutic agent(s) are mixed.

Mixing or compounding biocompatible polymer with therapeutic agent(s) and any additional additives to form a substantially homogenous mixture thereof may be performed with any device known in the art and conventionally used for mixing polymeric materials with additives.

Where thermoplastic materials are employed, a polymer melt may be formed by heating the biocompatible polymer, which can be mixed with various additives (e.g., therapeutic agent(s), inactive ingredients, etc.) to form a mixture. A common way of doing so is to apply mechanical shear to a mixture of the biocompatible polymer(s) and additive(s). Devices in which the biocompatible polymer(s) and additive(s) may be mixed in this fashion include devices such as single screw extruders, twin screw extruders, banbury mixers, high-speed mixers, ross kettles, and so forth.

Any of the biocompatible polymer(s) and various additives may be premixed prior to a final thermoplastic mixing and shaping process, if desired (e.g., to prevent substantial degradation of the therapeutic agent among other reasons).

For example, in various embodiments, a biocompatible polymer is precompounded with a radiographic agent (e.g., radio-opacifying agent) under conditions of temperature and mechanical shear that would result in substantial degradation of the therapeutic agent, if it were present. This pre-compounded material is then mixed with therapeutic agent under conditions of lower temperature and mechanical shear, and the resulting mixture is shaped into the active ingredient containing drug depot. Conversely, in another embodiment, the biocompatible polymer can be precompounded with the therapeutic agent under conditions of reduced temperature and mechanical shear. This precompounded material is then mixed with, for example, a radio-opacifying agent, also under conditions of reduced temperature and mechanical shear, and the resulting mixture is shaped into the drug depot.

The conditions used to achieve a mixture of the biocompatible polymer and therapeutic agent and other additives will depend on a number of factors including, for example, the specific biocompatible polymer(s) and additive(s) used, as well as the type of mixing device used.

As an example, different biocompatible polymers will typically soften to facilitate mixing at different temperatures. For instance, where a depot is formed comprising PLGA or PLA polymer, a radio-opacifying agent (e.g., bismuth subcarbonate), and a therapeutic agent prone to degradation by heat and/or mechanical shear (e.g., clonidine), in various embodiments, the PGLA or PLA can be premixed with the radio-opacifying agent at temperatures of about, for example, 150° C. to 170° C. The therapeutic agent is then combined with the premixed composition and subjected to further thermoplastic processing at conditions of temperature and mechanical shear that are substantially lower than is typical for PGLA or PLA compositions. For example, where extruders are used, barrel temperature, volumetric output are typically controlled to limit the shear and therefore to prevent substantial degradation of the therapeutic agent(s). For instance, the therapeutic agent and premixed composition can be mixed/compounded using a twin screw extruder at substantially lower temperatures (e.g., 100-105° C.), and using substantially reduced volumetric output (e.g., less than 30% of full capacity, which generally corresponds to a volumetric output of less than 200 cc/min). It is noted that this processing temperature is well below the melting points of certain active ingredients, such as an anti-inflammatory and analgesic because processing at or above these temperatures will result in substantial therapeutic agent degradation. It is further noted that in certain embodiments, the processing temperature will be below the melting point of all bioactive compounds within the composition, including the therapeutic agent. After compounding, the resulting depot is shaped into the desired form, also under conditions of reduced temperature and shear.

In other embodiments, biodegradable polymer(s) and one or more therapeutic agents are premixed using non-thermoplastic techniques. For example, the biocompatible polymer can be dissolved in a solvent system containing one or more solvent species. Any desired agents (for example, a radio-opacifying agent, a therapeutic agent, or both radio-opacifying agent and therapeutic agent) can also be dissolved or dispersed in the solvents system. Solvent is then removed from the resulting solution/dispersion, forming a solid material. The resulting solid material can then be granulated for further thermoplastic processing (for example, extrusion) if desired.

As another example, the therapeutic agent can be dissolved or dispersed in a solvent system, which is then applied to a pre-existing drug depot (the pre-existing drug depot can be formed using a variety of techniques including solution and thermoplastic processing techniques, and it can comprise a variety of additives including a radio-opacifying agent and/or viscosity enhancing agent), whereupon the therapeutic agent is imbibed on or in the drug depot. As above, the resulting solid material can then be granulated for further processing, if desired.

Typically, an extrusion processes may be used to form the drug depot comprising a biocompatible polymer(s), therapeutic agent(s) and radio-opacifying agent(s). Co-extrusion may also be employed, which is a shaping process that can be used to produce a drug depot comprising the same or different layers or regions (for example, a structure comprising one or more polymeric matrix layers or regions that have permeability to fluids to allow immediate and/or sustained drug release). Multi-region depots can also be formed by other processing and shaping techniques such as co-injection or sequential injection molding technology.

In various embodiments, the depot that may emerge from the thermoplastic processing (e.g., pellet, strip, etc.) is cooled. Examples of cooling processes include air cooling and/or immersion in a cooling bath. In some embodiments, a water bath is used to cool the extruded depot. However, where a water-soluble therapeutic agent such as active ingredients are used, the immersion time should be held to a minimum to avoid unnecessary loss of therapeutic agent into the bath.

In various embodiments, immediate removal of water or moisture by use of ambient or warm air jets after exiting the bath will also prevent re-crystallization of the drug on the depot surface, thus controlling or minimizing a high drug dose "initial burst" or "bolus dose" upon implantation or insertion if this is release profile is not desired. Thus, a sustained release region of the drug depot may, in various embodiments, be made by immediately removal of water or moisture.

In various embodiments, the drug depot can be prepared by mixing or spraying the drug with the polymer and then molding the depot to the desired shape. In various embodiments, active ingredients are used and mixed or sprayed with the PLGA or PEG550 polymer, and the resulting depot may be formed by extrusion and dried.

The drug depot may also comprise combining a biocompatible polymer and a therapeutically effective amount of at least one analgesic agent or pharmaceutically acceptable salt thereof and at least one anti-inflammatory agent or pharmaceutically acceptable salt thereof and forming the implantable drug depot from the combination.

The anchor can be made the same way as the drug depot. Various techniques are available for forming the anchor, for example, from a biocompatible polymer(s), including the solution processing techniques and/or thermoplastic processing techniques.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A drug depot for implantation at or near a target tissue site beneath the skin of a patient, the drug depot comprising a solid body comprising one or more immediate release layers that release a bolus dose of a drug and one or more sustained release layers that release a therapeutically effective amount of the drug and a polymer having an average molecular weight of about 10,000 to about 100,000, wherein the drug depot is attached to at least one line comprising a shape memory polymer and a coating comprising a drug, the at least one line having a distal end and a proximal end, the proximal end of the line attached to the drug depot; and the distal end of the line is attached to an anchor that is configured to limit movement of the drug depot at or near the target tissue site, wherein the anchor comprises a pellet that is rotatably attached to the line, the pellet comprising a cylindrical shape having a distal end defining a planar surface and a tapered proximal end, the pellet may be turned clockwise or counterclockwise when implanted so as to lodge the pellet at or near the target tissue site and the pellet comprising a polymer having an average molecular weight of about 10,000 to about 100,000, wherein the drug depot is capable of releasing the therapeutically effective amount of the drug over a period of at least one day, and wherein the line spaces the drug depot from the anchor by a distance of from about 0.1 mm to about 5 cm, and the line comprises a diameter smaller than the pellet and the drug depot.

2. A drug depot according to claim 1, wherein the anchor comprises a biodegradable pellet.

3. A drug depot according to claim 1, wherein the drug depot is biodegradable and the line is attached to a distal end of the drug depot.

4. A drug depot according to claim 1, wherein the target tissue site is an annular tear.

5. A drug depot according to claim 1, wherein the at least one line comprises a suture, yarn, thread, and/or wire.

6. A drug depot according to claim 5, wherein the line is a biodegradable suture.

7. A drug depot according to claim 6, wherein the suture is attached to the anchor at a point off center.

8. A drug depot according to claim 6, wherein the suture is attached to the drug depot and/or the anchor by a knot, rim, bead or clip.

9. A drug depot according to claim 1, wherein the drug depot, the at least one line and the anchor are biodegradable and the anchor degrades slower than the line and drug depot.

10. A drug depot according to claim 1, wherein the line spaces the drug depot from the anchor a distance of from about 0.5 mm to about 2 mm.

11. A drug depot according to claim 1, wherein the drug depot comprises an analgesic and an anti-inflammatory agent.

12. A drug depot according to claim 1, wherein the one or more immediate release layers comprises poly(lactide-co-glycolide) (PLGA), and the one or more sustain release layers comprises polylactide (PLA).

13. A drug depot according to claim 1, wherein the drug depot further comprises a pore forming agent.

14. A drug depot for implantation at or near a target tissue site beneath the skin of a patient, the drug depot comprising a solid body comprising one or more immediate release layers that release a bolus dose of a drug and one or more sustained release layers that release a therapeutically effective amount of the drug, and a biodegradable polymer having an average molecular weight of about 10,000 to about 100,000; wherein the drug depot is attached to at least one suture comprising a shape memory polymer and a coating comprising a drug, the at least one suture having a distal end and a proximal end, the proximal end of the suture attached to the drug depot; and wherein an anchor is attached to the distal end of the suture and configured to limit movement of the drug depot at or near the target tissue site, wherein the anchor comprises a pellet that is rotatably attached to the suture, the pellet comprising a cylindrical shape having a distal end defining a planar surface and a tapered proximal end, the pellet may be turned clockwise or counterclockwise when implanted so as to lodge the pellet at or near the target tissue site and the pellet comprising a polymer having an average molecular weight of about 10,000 to about 100,000, wherein the drug depot is capable of releasing the therapeutically effective amount of the drug over a period of at least one day, and wherein the suture spaces the drug depot from the anchor by a distance of from about 0.1 mm to about 5 cm and wherein the suture is biodegradable, degrades slower than said biodegradable polymer, and comprises a diameter smaller than the pellet and the drug depot, and the target tissue site is an annular tear.

15. A drug depot according to claim 14, wherein the anchor comprises a biodegradable pellet.

16. A drug depot according to claim 14, wherein the at least one suture is attached to a distal end of the drug depot.

17. A drug depot according to claim 14, wherein the suture is attached to the anchor at a point off center.

18. A drug depot according to claim 14 wherein the suture spaces the drug depot from the anchor a distance of from about 0.5 mm to about 2 mm.

19. A drug depot according to claim 14, wherein the drug depot comprises an analgesic and an anti-inflammatory agent.

20. A drug depot according to claim 14, wherein the anchor is biodegradable and the anchor degrades slower than the suture and drug depot.

* * * * *